(12) United States Patent
Lutz et al.

(10) Patent No.: US 10,470,810 B2
(45) Date of Patent: Nov. 12, 2019

(54) GUIDE WIRE CONTROL DEVICE

(71) Applicant: SWEMAC INNOVATION AB, Linköping (SE)

(72) Inventors: Christian Lutz, Heikendorf (DE); Klaus Dorawa, Schönkirchen (DE)

(73) Assignee: SWEMAC INNOVATION AB, Linkoping (SE)

( * ) Notice: Subject to any disclaimer, the term of this patent is extended or adjusted under 35 U.S.C. 154(b) by 94 days.

(21) Appl. No.: 15/531,474

(22) PCT Filed: Dec. 16, 2014

(86) PCT No.: PCT/EP2014/077890
§ 371 (c)(1),
(2) Date: May 30, 2017

(87) PCT Pub. No.: WO2016/095956
PCT Pub. Date: Jun. 23, 2016

(65) Prior Publication Data
US 2018/0368903 A1    Dec. 27, 2018

(51) Int. Cl.
*A61B 17/88*    (2006.01)

(52) U.S. Cl.
CPC ...... *A61B 17/8897* (2013.01); *A61B 17/8861* (2013.01); *A61B 17/8872* (2013.01)

(58) Field of Classification Search
CPC ..... A61B 17/8897; A61B 17/88; A61B 17/17; A61B 2017/00367
See application file for complete search history.

(56) References Cited

U.S. PATENT DOCUMENTS

| | | | | |
|---|---|---|---|---|
| 5,609,597 A | * | 3/1997 | Lehrer | A61B 17/0483 289/17 |
| 5,902,305 A | | 5/1999 | Beger et al. | |
| 5,902,306 A | * | 5/1999 | Norman | A61B 17/1697 606/104 |

(Continued)

FOREIGN PATENT DOCUMENTS

| | | |
|---|---|---|
| JP | 49048721 | 7/1947 |
| JP | 50123129 | 10/1975 |

(Continued)

*Primary Examiner* — Lynnsy M Summitt
*Assistant Examiner* — Tara Rose E Carter
(74) *Attorney, Agent, or Firm* — Tarolli, Sundheim, Covell & Tummino LLP

(57) ABSTRACT

A guide wire control device for advancing a guide wire into a body or a portion of the body, comprises a handle member (1), a lever (2) and a spring means (3). The spring means (3) holds the lever (2) relative to the handle member (1) such that the longitudinal axis of a through-hole (9) in the lever (2) is misaligned with the longitudinal axis of an elongate passage (4) in the handle member (1) for locking the guide wire control device to a guide wire (5) extending through said elongate passage and said through-hole. Pivotal movement of the lever (2) brings the longitudinal axis of the through-hole (9) into alignment or substantial alignment with the longitudinal axis of the elongate passage (4) for release of the guide wire (5). Pivotal movement of the lever (2) also brings the longitudinal axis of the through-hole (9) into renewed misalignment with the longitudinal axis of the elongate passage (4) for clamping of the guide wire (5).

14 Claims, 3 Drawing Sheets

(56) References Cited

U.S. PATENT DOCUMENTS

| | | |
|---|---|---|
| 7,011,635 B1 | 3/2006 | Delay |
| 2010/0042106 A1 | 2/2010 | Bryant et al. |
| 2010/0318137 A1 | 12/2010 | Stucki et al. |

FOREIGN PATENT DOCUMENTS

| | | |
|---|---|---|
| JP | 6179000 | 5/1986 |
| JP | 360613 | 6/1991 |

\* cited by examiner

GUIDE WIRE CONTROL DEVICE

RELATED APPLICATION

This application corresponds to PCT/EP2014/077890, filed Dec. 16, 2014, the subject matter, of which is incorporated herein by reference in its entirety.

TECHNICAL FIELD

The present invention relates to a guide wire control device for advancing a guide wire into a body or a portion of the body. The guide wire control device comprises a handle member, a lever and a spring means.

BACKGROUND OF THE INVENTION

Guide wires are used during various interventional medical procedures to navigate therapeutic devices to a treatment site within a body, such as within a bone for reducing a fracture in the bone. Accordingly, guide wires may be advanced into the canal of a broken long bone to align the bone fragments before reducing the bone fracture. The guide wires have a small diameter and in order to be able to advance them, some kind of handle is used to grip the guide wire and apply the necessary force for the advancement. The exterior of the guide wire is smooth and the instrument for the advancement may not leave marks on the exterior that damage the guide wire nor may the forces applied thereby result in that the guide wire is bent in any way.

Several types of guide wire control devices for advancing a guide wire are already known in the prior art. The purpose of a guide wire control device is to provide sufficient clamping force on the smooth exterior surface of the guide wire to be able to advance the guide wire. This is normally done by means of a press fit which generates sufficient friction to avoid slipping of the guide wire. To this end, a so called Jacob's chuck may be used. The Jacob's chuck is also known from drilling machines where it basically has the same function. Typically, three clamping jaws are tightened via a cone and thread mechanism. The clamping jaws are pressed together when a ring or nut is rotated. Another type is a collet chuck. The collet chuck is also pressed together onto the exterior of the guide wire via a cone, thereby generating a friction force. Both these prior art solutions have the drawback that they need to be tightened and untightened in order to generate the force for clamping the guide wire. This is a time-consuming procedure. Particularly in long bone nailing, the guide wires are long and must be gripped several times before they are fully inserted into the bone. Because of their length and small diameter, they cannot be gripped only at their ends. Doing so, will lead to kinking of the guide wire. Another drawback is that the guide wires slip easy because they are clamped at a large surface area. The intended use of the guide wires results in that they are often covered with blood and fat. These substances make it difficult for the chucks to transmit the necessary force. Also, the prior art instruments are difficult to disassemble for cleaning.

SUMMARY OF THE INVENTION

The object of the present invention is to provide a guide wire control device which eliminates or at least ameliorates the disadvantages of the prior art.

This object may be achieved by the subject matter of appended claim 1, i.e. by means of a guide wire control device as defined above, wherein the handle member is configured with an elongate passage which extends through the handle member in the longitudinal direction thereof and with a recess which extends in a substantially transverse direction relative to the elongate passage and which intersects said elongate passage, wherein the lever is pivotally mounted in the recess and configured to protrude out of said recess, wherein the part of the lever situated inside the recess is configured with a transverse through-hole, and wherein the spring means is configured to hold the lever relative to the handle member such that the longitudinal axis of the through-hole in the lever is misaligned with the longitudinal axis of the elongate passage in the handle member for locking of the guide wire control device to a guide wire extending through said elongate passage and said through-hole, to permit pivotal movement of the lever relative to the handle member in order to bring the longitudinal axis of the through-hole into alignment or substantial alignment with the longitudinal axis of the elongate passage in the handle member for release of a guide wire extending through said elongate passage and said through-hole such that the guide wire control device can be displaced relative to the guide wire, and to permit pivotal movement of the lever relative to the handle member in order to bring the longitudinal axis of the through-hole in the lever into misalignment with the longitudinal axis of the elongate passage for clamping of a guide wire extending through said elongate passage and said through-hole such that the guide wire can be advanced by means of the guide wire control device.

In a preferred embodiment of the present invention, the spring means of the guide wire control device is configured to permit pivotal movement of the lever relative to the handle member against the direction of the spring load of the spring means in order to bring the longitudinal axis of the through-hole into alignment or substantial alignment with the longitudinal axis of the elongate passage in the handle member for release of a guide wire extending through said elongate passage and said through-hole such that the guide wire control device can be displaced relative to the guide wire, and to permit further pivotal movement of the lever relative to the handle member against the direction of the spring load of the spring means in order to bring the longitudinal axis of the through-hole in the lever into misalignment with the longitudinal axis of the elongate passage for clamping of a guide wire extending through said elongate passage and said through-hole such that the guide wire can be advanced by means of the guide wire control device.

Thus, according to the preferred embodiment of the present invention, there is provided a guide wire control device which, when the lever occupies an inoperative position in which it is held by the spring means, permits locking of the guide wire control device to a guide wire which extends through the elongate passage in the handle member and through the through-hole in the lever with sufficient clamping force without damaging or bending the guide wire, which, when the lever occupies a first operative position into which it is pivotally moved by hand against the direction of the spring load of the spring means, permits displacement of the guide wire control device relative to the guide wire for moving the guide wire control device to another position for e.g. renewed gripping or engagement of the guide wire for further advancement thereof, and which, when the lever occupies a second operative position into which it is pivotally moved by hand against the direction of the spring load of the spring means, permits clamping of the guide wire such that the guide wire can be advanced by means of the guide wire control device.

The functions of the guide wire control device defined above can be achieved by a spring means which is configured to permit the lever to pivot, from its inoperative position for locking of the guide wire control device to a guide wire, to its two operating positions for release of the guide wire such that the guide wire control device can be displaced relative to the guide wire and for clamping of a guide wire such that the guide wire can be advanced by means of the guide wire control device respectively, by pivotal movements not only against the direction of the spring load of the spring means as defined above, but also in the direction of the spring load of the spring means or by pivotal movements against as well as in the direction of the spring load of the spring means.

With the guide wire control device according to the present invention, the guide wire control device can then be free to move along a guide wire or a high and adjustable clamping force can be achieved or when the guide wire control device is not manipulated, it can stay in position on the guide wire.

Since the handle member of the guide wire control device according to the present invention surrounds the guide wire, the guide wire control device allows advancement of the guide wire in the direction of the longitudinal axis of the guide wire, such that no bending moments are generated on the guide wire also for this reason.

Details of the preferred embodiments of the guide wire control device according to the present invention are defined in the depending claims.

Thus, thanks to the various specific constructions of the guide wire control device, quick and easy adjustment of the clamping force and quick handling of the device is possible.

BRIEF DESCRIPTION OF THE DRAWINGS

The present invention will hereinafter be further described by means of a non-limiting example with reference to the accompanying drawings, wherein.

It should be noted that the accompanying drawings are not necessarily drawn to scale and that the dimensions of some features may have been exaggerated for the sake of clarity.

DETAILED DESCRIPTION OF A PREFERRED EMBODIMENT

The present invention will in the following be exemplified by an embodiment. It should be realized however, that the embodiment is included in order to explain principles of the invention and not to limit the scope of the invention, defined by the appended claims.

Figure 1:
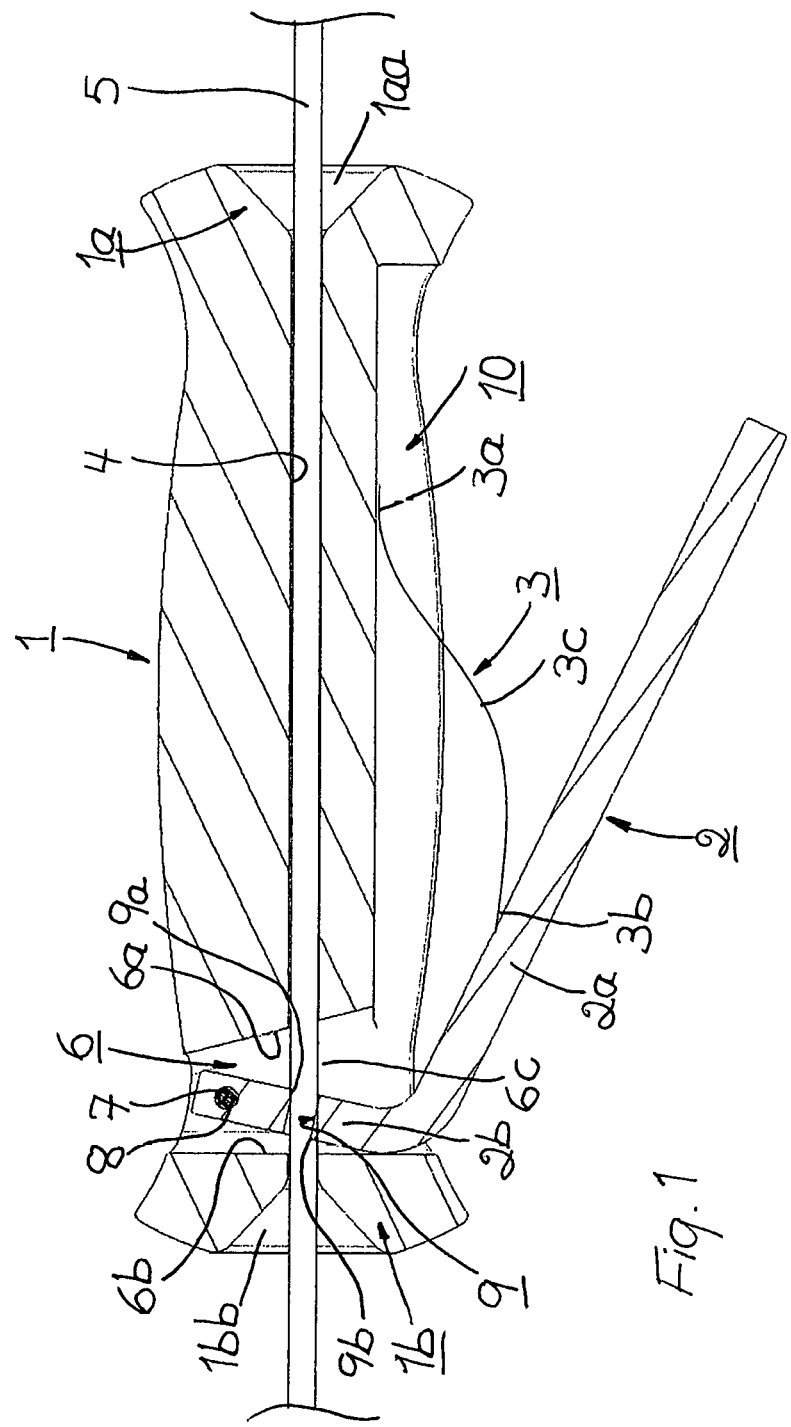
FIG. 1 is a schematic sectional view in the longitudinal direction of a guide wire control device according to the present invention in a first, inoperative position with unmanipulated lever.
Figure 2:
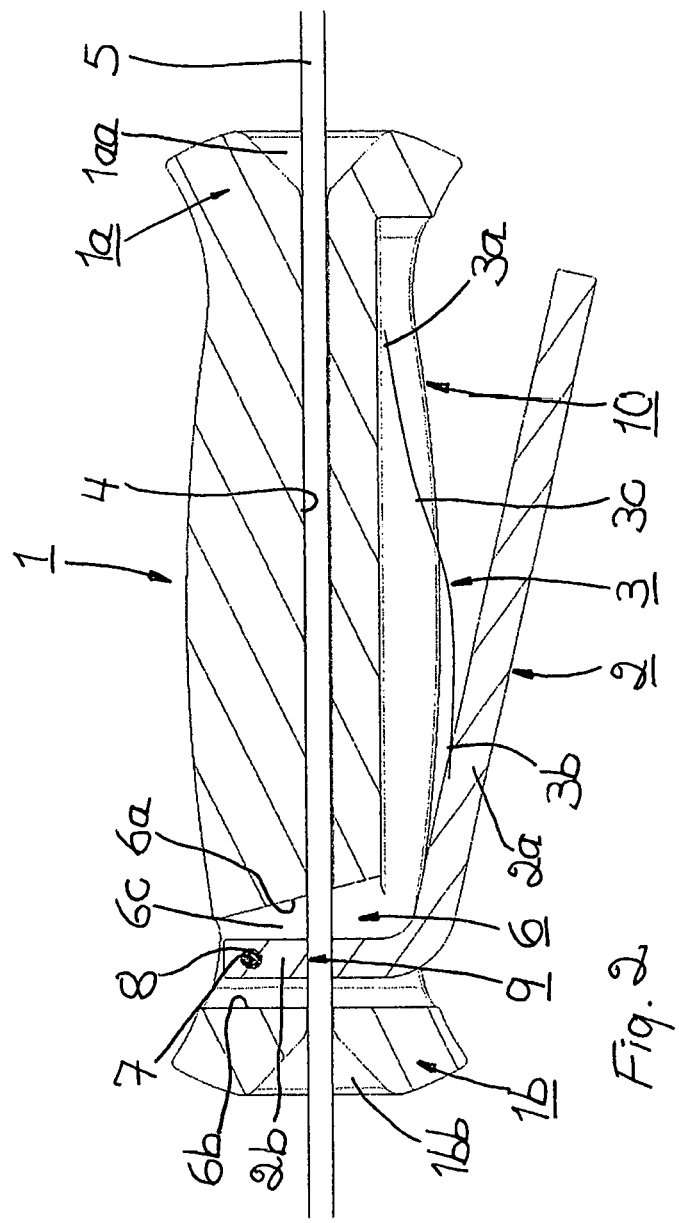
FIG. 2 is a schematic sectional view similar to FIG. 1 of the guide wire control device according to the invention in a second, operative position with manipulated lever.
Figure 3:
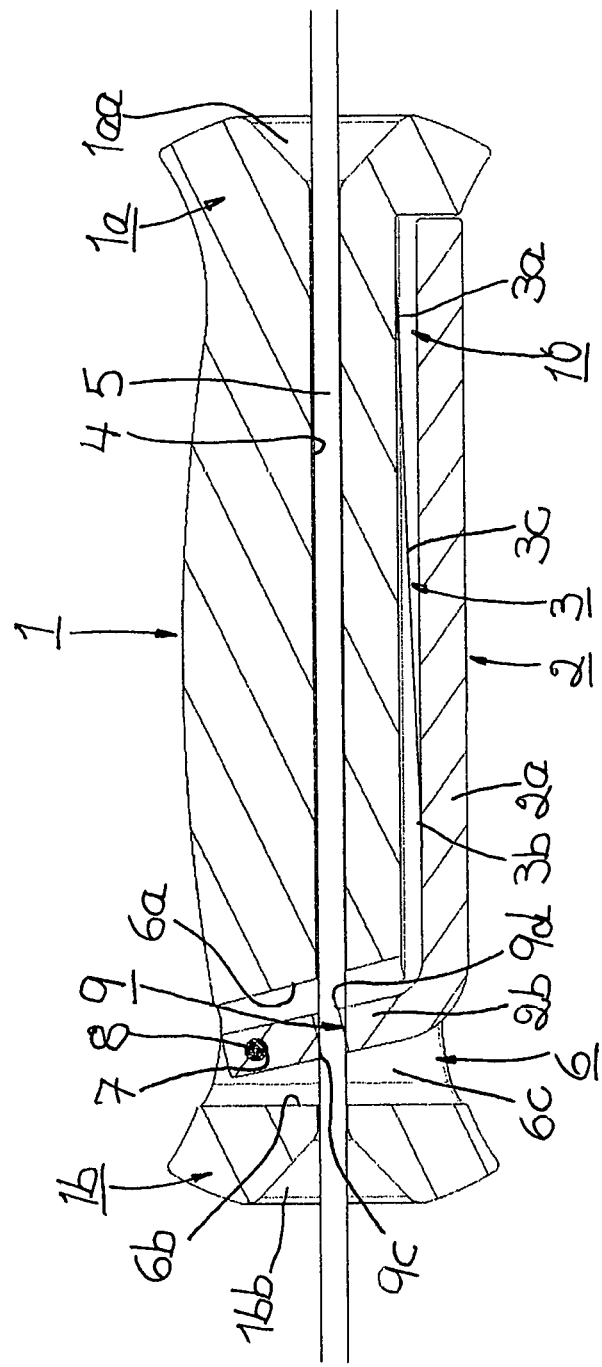
FIG. 3 is a schematic sectional view similar to FIGS. 1 and 2 of the guide wire control device according to the invention in a third, another operative position with manipulated lever.

FIGS. 1 to 3 all illustrate a preferred embodiment of a guide wire control device according to the present invention for advancing a guide wire into a body or a portion of the body. Thus, the guide wire control device comprises, generally seen, a handle member 1, a lever 2 and a spring means 3. In the drawings, the guide wire control device is illustrated with the lever 2 located under the handle member 1, such that the lever most probably is engaged and manipulated by means of the fingers of one hand of an operator, but the guide wire control device may of course also be used with the lever facing upwards, thereby being engaged and manipulated by the palm of a hand of the operator, or in any other direction. The guide wire control device may e.g. alternatively be used such that a guide wire is advanced into a body or body portion from above or from below or in any other preferred direction.

The handle member 1, indeed shaped as an ergonomically optimal handle to be gripped by a hand of an operator, is configured with an elongate passage 4. The elongate passage 4 extends through the handle member 1 in the longitudinal direction thereof, from a proximal end portion 1a of the handle member to a distal end portion 1b thereof if seen in the direction of intended advancement of a guide wire. The elongate passage 4 extends preferably centrally through the handle member 1. The elongate passage 4 is, as indicated, adapted to receive a guide wire 5 for advancement of the guide wire into a body or a portion of the body. For effective guiding of the guide wire 5 by means of the guide wire control device, it is necessary that the diameter of the elongate passage 4 is dimensioned as illustrated, i.e. only somewhat larger than the diameter of the guide wire for which it is intended. The handle member 1 is also configured with a recess 6 for the lever 2. The recess 6, which is located at the distal end of the handle member 1, extends in the illustrated embodiment through the entire handle member in the crosswise direction thereof, and thereby in a substantially transverse direction relative to the elongate passage 4. The recess 6 also intersects the elongate passage 4, i.e. the elongate passage opens into the recess at the proximal side 6a of said recess and continues at the distal side 6b of the recess.

The lever 2 is pivotally mounted in the recess 6. The lever 2 is also configured to protrude out of the recess 6. The lever 2 is in the illustrated embodiment angularly shaped, with the major part 2a thereof protruding out of the recess and extending along the handle member 1 at an angle thereto such that it will be easy to get hold of the lever while at the same time maintain a comfortable grip around the handle member, and with the minor part 2b of the lever situated inside the recess 6. With the major part 2a of the lever 2 situated outside the recess 6, it is easier to generate a sufficient clamping force for the intended purpose of the guide wire control device, i.e. the longer said part is, the higher the force. The minor part 2b of the lever 2 situated inside the recess 6 is at one end portion thereof configured with a bore 7 which is threaded onto a shaft 8 or alternatively, configured with a shaft 8 which is integral with the lever. The shaft 8 extends transverse to the recess 6 at an end thereof opposite to the end where the major part 2a of the lever 2 protrudes out of the recess, for pivotal movement of the lever about said shaft. To facilitate pivotal movement of the lever 2, the recess 6 expands towards the end thereof where the major part 2a of the lever 2 protrudes out of the recess, i.e. the proximal and distal sides 6a, 6b thereof diverge towards said end of the recess. The ends of the shaft 8 are attached to the lateral sides (of which the lateral side 6c is illustrated in the drawings) of the recess 6. The minor part 2b of the lever 2 situated inside the recess 6 is also configured with a through-hole 9 for a guide wire 5. The through-hole 9 is situated preferably centrally in said part and substantially in line with the elongate passage 4, such that a guide wire 5 can be moved into the elongate passage 4 from the proximal end portion 1a of the handle member 1, moved through the elongate passage, through the through-hole 9 in the minor part 2b of the lever 2 and finally into the elongate passage in the distal end portion 1b of the handle member. To facilitate insertion of the guide wire 5 into the handle member 1, the inlet end 1aa at the proximal end portion 1a of the handle member is preferably tapering in distal direction towards the elongate passage 4 and in order to prevent bending of the guide wire at the distal end portion 1b of the handle member, the outlet end 1bb at said distal end portion is preferably also tapering towards the elongate passage, i.e. in proximal direction.

The spring means has in the illustrated embodiment the form of a spring plate 3 with a curved or bent end 3a which is slidably engaging the handle member 1 on the side thereof facing the major part 2a of the lever 2, and an opposite end 3b which preferably is straight and extends angularly relative to the intermediate major part 3c of the spring plate and which is fixedly attached to the lever 2. The intermediate major part 3c of the spring plate 3 has in the illustrated embodiment an elongate S-shape. The spring means 3 is configured to hold the lever 2 relative to the handle member 1 such that the longitudinal axis of the through-hole 9 in the lever is misaligned with the longitudinal axis of the elongate passage 4 in the handle member. Thus, if and when the lever 2 is not manipulated in any way, the spring means 3 holds the lever 2 in a first, inoperative position relative to the handle member 1 in which the guide wire control device is locked to a guide wire 5 extending through said elongate passage and said through-hole, i.e. a kind of self-retention. This first, inoperative position is illustrated in FIG. 1.

The spring means 3 is further configured to permit pivotal movement of the lever 2 and this is in the illustrated embodiment accomplished by pivoting said lever against the direction of the spring load of said spring means.

Thus, from the first, inoperative position according to FIG. 1, a pivotal movement of the lever 2 relative to the handle member 1 can be performed such that the lever attains the position illustrated in FIG. 2, i.e. a pivotal movement of the lever towards the handle member. This pivotal movement of the lever 2 against the direction of the spring load of the spring means 3 brings the longitudinal axis of the through-hole 9 into alignment or substantial alignment with the longitudinal axis of the elongate passage 4. Thus, by manipulating the lever 2 from the inoperative position according to FIG. 1 to this second, operative position relative to the handle member 1 according to FIG. 2, it is possible to release a guide wire 5 extending through said elongate passage 4 and said through-hole 9 such that the guide wire control device can be displaced relative to the guide wire. Preferably, the guide wire control device is then moved along the guide wire 5 in a direction against the direction of advancement of the guide wire, i.e. in proximal direction, for renewed gripping or engagement of the guide wire for further advancement thereof or for removing the guide wire control device from the guide wire when the guide wire has been advanced to the desired position. During manipulation of the lever 2 from the inoperative position according to FIG. 1 to the operative position relative to the handle member 1 according to FIG. 2, the curved or bent end 3a of the spring means 3 slides, as is apparent from said FIGS. 1 and 2, in proximal direction along the handle member 1 and the intermediate major part 3c of the spring means (spring plate) is straightened.

Furthermore, directly from the first, inoperative position according to FIG. 1, which is the normal position when advancement of a guide wire 5 is about to begin, or from the second, operative position according to FIG. 2, which is the position of the guide wire control device when advancement already has begun and the guide wire control device as mentioned is moved in proximal direction for renewed gripping or engagement of the guide wire for continued advancement thereof, a pivotal movement of the lever 2 relative to the handle member 1 can be performed such that the lever attains the position illustrated in FIG. 3, i.e. a further pivotal movement of the lever further towards the handle member and according to FIG. 3 very close to said handle member. This additional pivotal movement of the lever 2 against the direction of the spring load of the spring means 3 brings the longitudinal axis of the through-hole 9 into another misalignment with the longitudinal axis of the elongate passage 4. Thus, by manipulating the lever 2 from the inoperative position according to FIG. 1 or from the second, operative position according to FIG. 2 to this third, operative position relative to the handle member 1 according to FIG. 3, it is possible to engage or clamp a guide wire 5 extending through said elongate passage 4 and said through-hole 9 with sufficient clamping force for advancing the guide wire into a body or a portion of the body without bending said guide wire. During manipulation of the lever 2 from the inoperative position according to FIG. 1 or from the second, operative position according to FIG. 2 to the operative position relative to the handle member 1 according to FIG. 3, the curved or bent end 3a of the spring means 3 slides, as is apparent from said FIGS. 1, 2 and 3, further in proximal direction along the handle member 1 and the intermediate major part 3c of the spring means (spring plate) has attained an almost straight configuration.

To facilitate the proximal sliding movements of the curved or bent end 3a of the spring means 3 during said manipulations of the lever 2 without risking that the spring means loses its engagement with the handle member, said end of the spring means is preferably slidably received in an elongate recess 10 which extends in the longitudinal direction of the handle member 1. In the illustrated embodiment of the guide wire control device, the recess 6 for the lever 2 and the recess 10 for the spring means 3 are integral and unite where the major part 2a of the lever 2 protrude out of the recess 6 therefor.

If the manipulation of the lever 2 ceases, i.e. the lever is released, the spring means automatically returns said lever to its inoperative position according to FIG. 1 irrespective of whether the guide wire control device is in the operative position according to FIG. 2 or in the operative position according to FIG. 3, and brings the lever to its inoperative position relative to the handle member 1 and holds it there such that the guide wire control device is locked to a guide wire 5 for self-retention of the guide wire control device.

Since the lever 2 by means of the spring means 3 is held in the inoperative position or upon release thereof is automatically returned to its inoperative position according to FIG. 1, insertion of a guide wire 5 may be facilitated if the lever from the inoperative position is pivoted against the direction of the spring load of the spring means such that the longitudinal axis of the through-hole 9 is brought into alignment or substantial alignment with the longitudinal axis of the elongate passage 4 as illustrated in FIG. 3.

The embodiment of the guide wire control device of FIGS. 1 to 3, is a good example of how the objects of the present invention can be realized in a simple and effective manner. Accordingly, in the illustrated embodiment of FIGS.

1 to 3, the diameter of the through-hole 9 in the part 2b of the lever 2 situated inside the recess 6 is dimensioned relative to the diameter of the guide wire 5 such that two diametrically opposed edges 9a and 9b or 9c and 9d at said through-hole will engage the guide wire during any misalignment of the longitudinal axis of the through-hole relative to the longitudinal axis of the elongate passage 4 in the handle member without negatively affecting the guide wire by e.g. damaging the exterior of the guide wire or bending the guide wire.

This means that the upper proximal edge 9a and the diametrically opposed lower distal edge 9b at the through-hole 9 engage the guide wire 5 preferably only when the longitudinal axis of the through-hole is misaligned with the longitudinal axis of the elongate passage 4 as illustrated in FIG. 1 and the guide wire control device thereby is locked to the guide wire 5 for self-retention of the guide wire control device. This also means that the upper distal edge 9c and the diametrically opposed lower proximal edge 9d at the through-hole 9 engage the guide wire 5 preferably only when the longitudinal axis of the through-hole is misaligned with the longitudinal axis of the elongate passage 4 as illustrated in FIG. 3 and the guide wire thereby is clamped by the guide wire control device for advancement of the guide wire by means of the guide wire control device. When none of said edges 9a, 9b, 9c, 9d at the through-hole 9 engages the guide wire 5 and the longitudinal axis of the through-hole is aligned or substantially aligned with the longitudinal axis of the elongate passage 4, as illustrated in FIG. 2, the guide wire control device is displaceable without friction relative to the guide wire for said renewed gripping or engagement of the guide wire for further advancement thereof or for removing the guide wire control device from the guide wire.

Thus, the above-mentioned safe and effective function of the guide wire control device without damaging or bending the guide wire 5 is achieved while two opposed edges 9a, 9b at the through-hole in the lever 2, from a position in which they engage the guide wire with a small clamping force (see FIG. 1), can be brought into a position without engagement with the guide wire and while instead two other opposed edges 9c, 9d can be brought from a position without engagement of the guide wire to a position in which they engage the guide wire with a substantial clamping force (see FIG. 3), or all of said edges are brought into a position with a very small or substantially unnoticeable or even non-existing engagement of the guide wire (see FIG. 2), depending on how much the lever is pivoted towards the handle member 1. The edges function as friction cones, generating an adjustable frictional engagement with the guide wire. The friction force is thanks to the respective cooperating two edges concentrated to a very small area. The small area may if desired result in a very high clamping force and thereby a more reliable prevention against slipping.

Also, as mentioned above, it should be noted that the functions of the guide wire control device defined above can be achieved by a spring means which is configured to permit the lever to pivot, from its inoperative position for locking of the guide wire control device to a guide wire, to its two operating positions for release of the guide wire such that the guide wire control device can be displaced relative to the guide wire and for clamping of a guide wire such that the guide wire can be advanced by means of the guide wire control device respectively, by pivotal movements not only against the direction of the spring load of the spring means, but also in the direction of the spring load of the spring means or by pivotal movements against the direction of the spring load of the spring means as well as in the direction of the spring force of the spring means.

Accordingly, within the scope of the present invention, it is possible to configure at least the spring means 3, possibly also the lever 2, such that said spring means permits pivotal movements of the lever from its inoperative position to its two operative positions in the direction of the spring load of the spring means, i.e. away from the handle member 1. It is e.g. possible to configure the spring means 3 such that the lever 2 in its inoperative position is situated as in FIG. 3 and such that the lever then can be pivoted in the direction of the spring load of the spring means, away from the handle member 1, to the operative positions according to FIG. 2 and FIG. 1.

This means, with reference to FIGS. 1 to 3, that the upper distal edge 9c and the diametrically opposed lower proximal edge 9d at the through-hole 9 engage the guide wire 5 preferably only when the longitudinal axis of the through-hole is misaligned with the longitudinal axis of the elongate passage 4 as illustrated in FIG. 3 and the guide wire control device thereby is locked to the guide wire 5 for self-retention of the guide wire control device. This also means that the upper proximal edge 9a and the diametrically opposed lower distal edge 9b at the through-hole 9 engage the guide wire 5 preferably only when the longitudinal axis of the through-hole is misaligned with the longitudinal axis of the elongate passage 4 as illustrated in FIG. 1 and the guide wire thereby is clamped by the guide wire control device for advancement of the guide wire by means of the guide wire control device. When none of said edges 9a, 9b, 9c, 9d at the through-hole 9 engages the guide wire 5 and the longitudinal axis of the through-hole is aligned or substantially aligned with the longitudinal axis of the elongate passage 4, as illustrated in FIG. 2, the guide wire control device is displaceable without friction relative to the guide wire for said renewed gripping or engagement of the guide wire for further advancement thereof or for removing the guide wire control device from the guide wire.

It is also within the scope of the present invention possible to configure at least the spring means 3, possibly also the lever 2, such that said spring means permits pivotal movement of the lever from its inoperative position to the operative position for release of the guide wire 5 such that the guide wire control device can be displaced relative to the guide wire, against the direction of the spring load of the spring means, i.e. towards the handle member 1, and such that said spring means permits pivotal movement of said lever to the operative position for clamping of a guide wire such that the guide wire can be advanced by means of the guide wire control device, in the direction of the spring load of the spring means, i.e. away from the handle member. It is e.g. possible to configure the spring means 3 such that the lever 2 in its inoperative position is situated as in FIG. 1, such that the lever can be pivoted against the direction of the spring load of the spring means, towards the handle member 1, to the operative position according to FIG. 2 (or according to FIG. 3 if the through-hole in the minor part of the lever allows it) and such that the lever can be pivoted in the direction of the spring load of the spring means, away from the handle member, to an operative position beyond the position of FIG. 1 which is not illustrated in the drawings.

This means, with reference to FIGS. 1 to 3, that the upper proximal edge 9a and the diametrically opposed lower distal edge 9b at the through-hole 9 engage the guide wire 5 when the longitudinal axis of the through-hole is misaligned with the longitudinal axis of the elongate passage 4 as illustrated in FIG. 1 and the guide wire control device thereby is locked to the guide wire 5 for self-retention of the guide wire control device. This also means that said upper proximal edge 9a and the diametrically opposed lower distal edge 9b at the through-hole 9 engage the guide wire 5 also when the longitudinal axis of the through-hole is misaligned with the longitudinal axis of the elongate passage 4 as illustrated in FIG. 1 and the guide wire thereby is clamped by the guide wire control device for advancement of the guide wire by means of the guide wire control device. The clamping force however, is here preferably stronger, i.e. the lever 2 is situated, as mentioned, in an operative position beyond the position of FIG. 1 which is not illustrated in the drawings.

When said edges 9a, 9b at the through-hole 9 does not engage the guide wire 5 and the longitudinal axis of the through-hole is aligned or substantially aligned with the longitudinal axis of the elongate passage 4, as illustrated in FIG. 2, the guide wire control device is displaceable without friction relative to the guide wire for said renewed gripping or engagement of the guide wire for further advancement thereof or for removing the guide wire control device from the guide wire.

It is also within the scope of the present invention possible to configure the lever 2 and the spring means 3 such that said spring means permits pivotal movement of said lever from its inoperative position to the operative position for release of the guide wire 5 such that the guide wire control device can be displaced relative to the guide wire, in the direction of the spring load of the spring means, i.e. away from the handle member 1, and such that said spring means permits pivotal movement of said lever to the operative position for clamping of a guide wire such that the guide wire can be advanced by means of the guide wire control device, against the direction of the spring load of the spring means, i.e. towards the handle member. By e.g. altering the through-hole 9 in the minor part 2b of the lever 2 from extending transverse through said minor part to extend at an angle thereto such that in FIG. 1 the other two diametrically opposed edges 9c, 9d engage the guide wire when the lever is in the inoperative position, it is possible, from the position according to FIG. 1, pivot the lever in the direction of the spring load of the spring means 3, away from the handle member 1, for release of the guide wire such that the guide wire control device can be displaced relative to the guide wire and to pivot the lever against the direction of the spring load of the spring means, towards the handle member, for clamping of a guide wire such that the guide wire can be advanced by means of the guide wire control device.

This means, again with reference to FIGS. 1 to 3, that the upper distal edge 9c and the diametrically opposed lower proximal edge 9d at the through-hole 9 engage the guide wire 5 when the longitudinal axis of the through-hole is misaligned with the longitudinal axis of the elongate passage 4, as illustrated in FIG. 3 but with the lever 2 in another position, and the guide wire control device thereby is locked to the guide wire 5 for self-retention of the guide wire control device. This also means that said upper distal edge 9c and the diametrically opposed lower proximal edge 9d at the through-hole 9 engage the guide wire 5 also when the longitudinal axis of the through-hole is misaligned with the longitudinal axis of the elongate passage 4 as illustrated in FIG. 3 and the guide wire thereby is clamped by the guide wire control device for advancement of the guide wire by means of the guide wire control device. When said edges 9c, 9d at the through-hole 9 does not engage the guide wire 5 and the longitudinal axis of the through-hole is aligned or substantially aligned with the longitudinal axis of the elongate passage 4, as illustrated in FIG. 2, the guide wire control device is displaceable without friction relative to the guide wire for said renewed gripping or engagement of the guide wire for further advancement thereof or for removing the guide wire control device from the guide wire.

In the two former of the above-mentioned alternative embodiments, it is possible to configure the spring means 3 and/or its attachments to the handle member 1 and the lever 2 respectively, such that when the lever 2 is pivoted away from the handle member 1 to a position beyond the position in FIG. 1, said spring means can be bent over in the sense that the curved or bent end 3a thereof slides in the recess 10 therefor in the distal direction along the handle member 1 until it passes a balance position and thereby locks the lever in a position in which a guide wire 5 can be clamped by the guide wire control device for advancement of the guide wire by means of the guide wire control device, i.e. the lever does not automatically return to its inoperative position when it is released.

In all the above-mentioned alternative embodiments it may on the other hand be advantageous if there is a stop means for the pivotal movement of the lever in the direction of the spring force of the spring means, away from the handle member. Such a stop means may be provided e.g. in the recess for the spring means, preventing excessive slidable displacement in the recess in distal direction of the end of the spring means located therein.

In the illustrated embodiment of the guide wire control device, the handle member 1 is configured to be made up of two parts which can be disassembled for cleaning of the interior thereof and for maintenance or exchange of the lever 2 and/or the spring means 3. However, only one of the parts defining the handle member 1 is shown in the drawings. Assembly and disassembly of the two parts constituting the handle member 1 can be achieved by any suitable means.

Further modifications of the present invention within the scope of the appended claims are feasible without departing from the idea and object of the invention. As such, the present invention should not be considered as limited by the embodiments described above or by the figures illustrating these embodiments. Rather, the full scope of the invention should be determined by the appended claims with reference to the description and drawings. Thus, the relationship between the diameters of the through-hole and guide wire respectively, may vary. It should be noted however, that the larger the diameter of the through-hole is relative to the diameter of the guide wire, the more the lever need to be pivoted for the edges of the through-hole in said minor part of the lever to come in contact with the guide wire in order to fulfill their intended functions. Spring means having different spring loads may also be used, depending e.g. on the thickness (diameter) of the guide wire and thereby also of the size of the lever and handle member and the through-hole as well as the elongate passage respectively, therein.

The invention claimed is:

1. Guide wire control device for advancing a guide wire into a body or a portion of the body, said guide wire control device comprising
a handle member (1), a lever (2) and a spring means (3),
wherein the handle member (1) is configured with an elongate passage (4) which extends through the handle member (1) in a longitudinal direction thereof and with a transverse recess (6) which extends in a substantially transverse direction relative to the elongate passage (4) and which intersects said elongate passage (4),
wherein the lever (2) is pivotally mounted in the transverse recess (6) and configured to protrude out of said transverse recess (6), wherein a part (2b) of the lever (2) situated inside the transverse recess (6) is configured with a transverse through-hole (9), and wherein the spring means (3) is configured to hold the lever (2) relative to the handle member (1) such that a longitudinal axis of the through-hole (9) in the lever (2) is misaligned with a longitudinal axis of the elongate passage (4) in the handle member (1) so that two edges at the through hole (9) engage a guide wire (5) extending through the elongated passage (4) and the through-hole (9) to lock the guide wire control device to the guide wire (5), to permit pivotal movement of the lever (2) relative to the handle member (1) in order to bring the longitudinal axis of the through-hole (9) into alignment or substantial alignment with the longitudinal axis of the elongate passage (4) so that the edges at the through-hole (9) disengage a guide wire (5) extending through the elongate passage (4) and the through-hole (9) to release the guide wire (5) such that the guide wire control device can be displaced relative to the guide wire (5), and to permit pivotal movement of the lever (2) relative to the handle member (1) in order to bring the longitudinal axis of the through-hole (9) into misalignment with the longitudinal axis of the elongate passage (4) so that two edges at the through hole (9) engage a guide wire (5) extending through the elongated passage (4) and the through-hole (9) to clamp the guide wire (5) such that the guide wire (5) can be advanced by the guide wire control device.

2. Guide wire control device according to claim 1, wherein the spring means (3) is configured to permit pivotal movement of the lever (2) relative to the handle member (1) against a direction of the spring load of the spring means (3) in order to bring the longitudinal axis of the through-hole (9) into alignment or substantial alignment with the longitudinal axis of the elongate passage (4) for release of a guide wire (5) extending through said elongate passage (4) and said through-hole (9) such that the guide wire control device can be displaced relative to the guide wire (5), and to permit further pivotal movement of the lever (2) relative to the handle member (1) against the direction of the spring load of the spring means (3) in order to bring the longitudinal axis of the through-hole (9) into misalignment with the longitudinal axis of the elongate passage (4) for clamping of a guide wire (5) extending through said elongate passage (4) and said through-hole (9) such that the guide wire (5) can be advanced by the guide wire control device.

3. Guide wire control device according to claim 2, wherein the spring means (3) is configured to automatically return the lever (2) to the position where the longitudinal axis of the through-hole (9) in the lever (2) is misaligned with the longitudinal axis of the elongate passage (4) in the handle member (1) for locking of the guide wire control device to a guide wire (5) extending through said elongated passage (4) and said through-hole (9) when said lever (2) is released after pivotal movement thereof in or against the direction of the spring load of the spring means (3).

4. Guide wire control device according to claim 2, wherein the spring means (3) is configured to permit pivotal movement of the lever (2) relative to the handle member (1) in or against the direction of the spring load of said spring means (3) in order to bring the longitudinal axis of the through-hole (9) into alignment or substantial alignment with the longitudinal axis of the elongate passage (4) for insertion of a guide wire (5) into said elongate passage (4) and said through-hole (9).

5. Guide wire control device according to claim 2, wherein a diameter of the through-hole (9) in the part (2a) of the lever (2) situated inside the transverse recess (6) is dimensioned relative to a diameter of a guide wire (5) extending through the elongate passage (4) and said through-hole (9) such that two diametrically opposed edges (9a and 9b or 9c and 9d) at said through-hole (9) will engage the guide wire (5) during any misalignment of the longitudinal axis of the through-hole (9) relative to the longitudinal axis of the elongate passage (4) in the handle member (1).

6. Guide wire control device according to claim 5, wherein the diameter of the through-hole (9) in the part (2a) of the lever (2) situated inside the transverse recess (6) is dimensioned relative to the diameter of a guide wire (5) extending through the elongate passage (4) and said through-hole (9) such that two diametrically opposed edges (9a, 9b or 9c, 9d) at said through-hole (9) will engage the guide wire (5) during misalignment of the longitudinal axis of the through-hole (9) relative to the longitudinal axis of the elongate passage (4) in the handle member (1) for locking of the guide wire control device to the guide wire (5).

7. Guide wire control device according to claim 6, wherein the diameter of the through-hole (9) in the part (2a) of the lever (2) situated inside the transverse recess (6) is dimensioned relative to the diameter of a guide wire (5) extending through the elongate passage (4) and said through-hole (9) such that two other diametrically opposed edges (9c, 9d or 9a, 9b) at said through-hole (9) will engage the guide wire (5) during misalignment of the longitudinal axis of the through-hole (9) relative to the longitudinal axis of the elongate passage (4) in the handle member (1) for clamping of the guide wire (5) such that the guide wire (5) can be advanced by the guide wire control device.

8. Guide wire control device according to claim 6, wherein the diameter of the through-hole (9) in the part (2a) of the lever (2) situated inside the transverse recess (6) is dimensioned relative to the diameter of a guide wire (5) extending through the elongate passage (4) and said through-hole (9) such that the same diametrically opposed edges (9a, 9b or 9c, 9d) at said through-hole (9) will engage the guide wire (5) during misalignment of the longitudinal axis of the through-hole (9) relative to the longitudinal axis of the elongate passage (4) in the handle member (1) for clamping of the guide wire (5) such that the guide wire (5) can be advanced by the guide wire control device.

9. Guide wire control device according to claim 1, wherein the spring means (3) is configured to permit pivotal movement of the lever (2) relative to the handle member (1) in a direction of the spring load of the spring means (3) in order to bring the longitudinal axis of the through-hole (9) into alignment or substantial alignment with the longitudinal axis of the elongate passage (4) for release of a guide wire (5) extending through said elongate passage (4) and said through-hole (9) such that the guide wire control device can be displaced relative to the guide wire (5), and to permit further pivotal movement of the lever (2) relative to the handle member (1) in the direction of the spring load of the spring means (3) in order to bring the longitudinal axis of the through-hole (9) into misalignment with the longitudinal axis of the elongate passage (4) for clamping of a guide wire (5) extending through said elongate passage (4) and said through-hole (9) such that the guide wire (5) can be advanced by the guide wire control device.

10. Guide wire control device according to claim 1, wherein the spring means (3) is configured to permit pivotal movement of the lever (2) relative to the handle member (1) against a direction of the spring load of the spring means (3)

in order to bring the longitudinal axis of the through-hole (9) into alignment or substantial alignment with the longitudinal axis of the elongate passage (4) for release of a guide wire (5) extending through said elongate passage (4) and said through-hole (9) such that the guide wire control device can be displaced relative to the guide wire (5), and to permit pivotal movement of the lever (2) relative to the handle member (1) in the direction of the spring load of the spring means (3) in order to bring the longitudinal axis of the through-hole (9) into misalignment with the longitudinal axis of the elongate passage (4) for clamping of a guide wire (5) extending through said elongate passage (4) and said through-hole (9) such that the guide wire (5) can be advanced by the guide wire control device.

11. Guide wire control device according to claim 1, wherein the spring means (3) is configured to permit pivotal movement of the lever (2) relative to the handle member (1) in a direction of the spring load of the spring means (3) in order to bring the longitudinal axis of the through-hole (9) into alignment or substantial alignment with the longitudinal axis of the elongate passage (4) for release of a guide wire (5) extending through said elongate passage (4) and said through-hole (9) such that the guide wire control device can be displaced relative to the guide wire (5), and to permit pivotal movement of the lever (2) relative to the handle member (1) against the direction of the spring load of the spring means (3) in order to bring the longitudinal axis of the through-hole (9) into misalignment with the longitudinal axis of the elongate passage (4) for clamping of a guide wire (5) extending through said elongate passage (4) and said through-hole (9) such that the guide wire (5) can be advanced by the guide wire control device.

12. Guide wire control device according to claim 1, wherein the spring means is configured as a spring plate (3) with one end (3a) thereof slidably engaging the handle member (1) and the opposite end (3b) thereof fixedly attached to the lever (2).

13. Guide wire control device according to claim 12, wherein said one end (3a) of the spring means (3) is slidably engaged in a longitudinal recess (10) in the handle member (1), said longitudinal recess (10) extending in the longitudinal direction of said handle member (1).

14. Guide wire control device according to claim 13, wherein the longitudinal recess (10) in which for the spring means (3) is slidably engaged is integral with the transverse recess (6) in which for the lever (2) is pivotally mounted.

* * * * *